US005614384A

United States Patent [19]

Kniskern et al.

[11] Patent Number: 5,614,384
[45] Date of Patent: Mar. 25, 1997

[54] HEPATITIS B VIRUS SURFACE PROTEINS WITH REDUCED HOST CARBOHYDRATE CONTENT

[75] Inventors: Peter J. Kniskern; Arpi Hagopian, both of Lansdale, Pa.

[73] Assignee: Merck & Co., Inc., Rahway, N.J.

[21] Appl. No.: 368,287

[22] Filed: Jan. 4, 1995

Related U.S. Application Data

[63] Continuation of Ser. No. 271,382, Jul. 6, 1994, abandoned, which is a continuation of Ser. No. 86,382, Jul. 1, 1993, abandoned, which is a continuation of Ser. No. 692,924, Apr. 29, 1991, abandoned.

[51] Int. Cl.$^6$ .............................. C12P 21/02; C12N 1/19; A61K 39/29

[52] U.S. Cl. .................................... 435/69.3; 435/254.21; 424/189.1

[58] Field of Search ......................... 424/189.1; 530/350, 530/395, 826; 435/69.3, 254.21

[56] References Cited

U.S. PATENT DOCUMENTS

| | | | |
|---|---|---|---|
| 4,707,542 | 11/1987 | Friedman et al. . | |
| 4,803,164 | 2/1989 | Hitzeman et al. | 435/69.3 |
| 4,816,564 | 3/1989 | Ellis et al. | 530/324 |
| 4,963,483 | 10/1990 | Ellis et al. | 435/69.3 |
| 5,133,961 | 7/1992 | Ellis et al. | 424/89 |
| 5,135,854 | 8/1992 | MacKay et al. | 435/69.1 |

FOREIGN PATENT DOCUMENTS

| | | |
|---|---|---|
| 0248637 | 12/1987 | European Pat. Off. . |
| 0314096 | 5/1989 | European Pat. Off. . |
| 0317254 | 5/1989 | European Pat. Off. . |
| 0344864 | 12/1989 | European Pat. Off. . |
| 0411896 | 2/1991 | European Pat. Off. . |
| 0414374 | 2/1991 | European Pat. Off. . |
| 0415565 | 3/1991 | European Pat. Off. . |
| 0431679 | 6/1991 | European Pat. Off. . |
| 88/3122/44 | 9/1988 | Japan . |

OTHER PUBLICATIONS

Itoh et al.; Biochemical and Biophysical Research Communications, vol. 141, No. 3; pp. 942–948; Dec. 30, 1986.
Peterson et al.; Proceedings of the National Academy of Sciences USA, vol. 74, No. 4; pp. 1530–1534; Apr. 1977.
Kniskern et al.; Hepatology, vol. 8, No. 1; pp. 82–87; 1988.
E. Jacobs, et al., Simultaneous synthesis and assembly of various hepatitis B surface proteins in *Saccharomyces cerevisiae*, Gene, 80: pp. 279–291 (1989).
Z. A. Janowicz, et al., Simultaneous Expression of the S and L Surface Antigens of Hepatitis B, and Formation of Mixed Particles in the Methylotrophic Yeast, *Hansenula polymorpha*, Yeast, 7: pp. 431–443 (1991).
M. Johnston & R. W. Davis, Sequences That Regulate the Divergent GAL1–GAL10 Promoter in *Saccharomyces cerevisiae*, Mol. & Cell. Bio. 4: pp. 1440–1448 (1984).
L. Ballou, et al., A mutation that prevents glucosylation of the lipid–linked oligosaccharide precursor leads to underglycosylation of secreted yeast invertase, Proc. Nat'l. Acad. Sci., USA 83: pp. 3081–3085 (1986).
P. K. Tsai, et al., Carbohydrate Structure of *Saccharomyces cerevisiae* mnn9 Mannoprotein, J. of Biol. Chem., 259: pp. 3805–3811 (1984).
L. Ballou, et al., *Saccharomyces cerevisiae* Mutants That Make Mannoproteins with a Truncated Carbohydrate Outer Chain, J. Biol. Chem. 255: pp. 5986–5991 (1980).
P. Hauser, et al., Immunological properties of recombinant HBsAg produced in yeast, Postgraduate Med. Journal, 63: pp. 83–91 (1987).
J. Petre, et al., Development of a hepatitis–B vaccine from transformed yeast cells, Postgraduate Med. Journal, 63: pp. 73–81 (1987).
C. Carty, et al., Galactose–Regulated Expression of Hepatitis B Surface Antigen by a Recombinant Yeast, Biotechnology Lett., 11: pp. 301–306 (1989).
R. W. Ellis, et al., Preparation and Testing of a Recombinant–Derived Hepatitis B Vaccine Consisting of Pre–S2+S Polypeptides, Viral Hep. & Liver Dis., pp. 1079–1086 (1988).
P. J. Kniskern, et al., A Candidate Vaccine for Hepatitis B Containing the Complete Viral Surface Protein, Hepatology, 8: pp. 82–87 (1988).
W. F. Carman et al., Vaccine–induced escape mutant of hepatitis B virus, Medical Science, 336: pp. 325–329 (1990).
D. R. Milich, et al., A Single 10–Residue Pre–S(1) Peptide Can Prime T Cell Help For Antibody Production To Multiple Epitopes Within The Pre–S(1), Pre–S(2), And S Regions of HBsAg, J. of Immunology, 138: pp. 4457–4465 (1987).
P. J. Kniskern, et al., The Application of Molecular Biology to the Development of Novel Vaccines, Immunobio. of Proteins & Peptides V, pp. 83–98 (1989).
P. Valenzuela, Antigen Engineering in Yeast: Synthesis and Assembly of Hybrid Hepatitis B Surface Antigen–Herpes Simplex 1 gD Particles, Biotechnology, 3: pp. 323–326 (1985).
Itoh, et al., Synthesis in Yeast of Hepatitis B Virus Surface Antigen Modified P31 Particles by Gene Modification, Biochem. Biophys. Res. Comm., 141: pp. 942–948 (1986).
Peterson, et al., Partial amino acid sequence of two major component polypeptides of hepatitis B surface antigen, Proc. Nat'l. Acad. Sci., 74: pp. 1530–1534 (1977).
Hilleman, Hepatitis B and AIDS and the promise for their control by vaccines, Vaccine, 6: pp. 175–179 (1988).

*Primary Examiner*—George C. Elliott
*Attorney, Agent, or Firm*—J. Mark Hand; Jack L. Tribble

[57] ABSTRACT

In order to produce hepatitis B virus (HBV) surface proteins in the form of particles with substantially reduced entrapped carbohydrate content, DNA encoding the HBV surface proteins was expressed in a recombinant yeast host which is deficient in its ability to glycosylate proteins. These HBV surface proteins display the antigenie sites genetically encoded by the S domain of the HBV virion envelope open reading frame and contains substantially reduced levels of entrapped carbohydrate when compared with HBsAg particles produced in "wild-type" yeast cells. These particles are useful as a vaccine for both the active and passive treatment or prevention of disease and/or infection caused by HBV or other agents serologically related to HBV.

5 Claims, 1 Drawing Sheet

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ACAAAACAAA                                                                                                          10

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AATTCAAGCT TACAAAACAA AATGCAGTGG                                                                                     30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTTCGAATGT TTTGTTTTAC GTCACCTTAA                                                                                     30

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATACATTTAA GCTTG                                                                                                    15

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TGTAAATTTC GAACCTAG                                                                                                 18

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AATTCAAGCT TACAAAACAA AATGGAGAAC ATCACATCAG GATTC                                                                    45

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTTCGAATGT TTTGTTTTAC CTCTTGTAGT GTAGTCCTAA GGATC    45

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AATTGTCGAC AGCTAGCTGA ATTCCCGGG    29

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AGCTCCCGGG AATTCAGCTA GCTGTCGAC    29

HEPATITIS B VIRUS SURFACE PROTEINS WITH REDUCED HOST CARBOHYDRATE CONTENT

This is a continuation of application Ser. No. 08/271,382, filed Jul. 6, 1994, abandoned, which was a continuation of application Ser. No. 08/086,382, filed Jul. 1, 1993, abandoned, which was a continuation of application Ser. No. 08/692,924, filed Apr. 29, 1991, abandoned.

BACKGROUND OF THE INVENTION

Hepatitis B virus (HBV) is the infectious agent responsible for several varieties of human liver disease. Many individuals who are infected by HBV suffer through an acute phase of disease, which is followed by recovery. However, a percentage of infected individuals fail to clear their infection, thereby becoming chronic carriers of the infection. HBV infection is endemic in many parts of the world, with a high incidence of infection occurring perinatally from chronically infected mothers to their newborns who themselves often remain chronically infected. The number worldwide has been estimated at over three hundred million. From this pool of carriers, hundreds of thousands die annually from the long-term consequences of chronic hepatitis B (cirrhosis and/or hepatocellular carcinoma).

The hepatitis B delta virus is an agent which, during coinfection with HBV, is responsible for an acute fulminating disease with a generally fatal resolution. The delta virus does not encode (from its own genetic material) proteins which serve as the virion envelope; rather, the virus encapsidates with the envelope proteins encoded by the coinfecting HBV, thereby sharing a close structural and immunologic relationship with the HBV proteins which are described below. It is unknown at this time whether other infectious agents share similar relationships with HBV. However, it is clear that proteins with expanded breadth of serologic reactivity or enhanced immunogenic potency would be useful in systems for diagnosis or prevention (or treatment) of diseases (or infections) by a class of agents with even slight or partial antigenic cross-reactivity with HBV.

The HB virion is composed of two groups of structural proteins, the core proteins and the envelope or surface proteins. In addition to being the major surface proteins or the virion, i.e., Dane particle, the envelope proteins also are the major constituents of Australia antigen, or 22 nm particles. These envelope proteins are the translational products of the large vital open reading frame (ORF) encoding at least 389 amino acids (aa). This ORF is demarcated into three domains, each of which begins with an ATG codon that is capable of functioning as a translational initiation site in vivo. These domains are referred to as preS1 (108 aa), preS2 (55 aa), and S (226 aa) in their respective 5'-3' order in the gens. Thus, these domains define three polypeptides referred to as S or HBsAg (226 aa), preS2+S (281 aa), and preS1+preS2+S (389 aa), also referred to as p24/gp27, p30/gp33/gp36 and p39/gp42 respectively (as well as the major, middle and large proteins).

The envelope proteins of HBV are glycoproteins with carbohydrate side chains (glycans) attached by N-glycosidic linkages to defined peptide recognition sites. [Heermann et al., *J. Virol.* 52, 396 (1984) and Stibbe et al., *J. Virol.* 46,626 (1983)]. Thus, the HBV polypeptides produced during natural infection comprise the species p24/gp27 (the S polypeptide and its glycosylated derivative), gp33/gp36 (the preS2+S polypeptide glycosylated in the preS2 domain only and the same polypeptide glycosylated in the S as well as the preS2 domain), and p39/gp42 (the preS1+preS2+S peptide and its derivative glycosylated in the preS1 domain). Currently available plasma-derived vaccines are composed of proteins containing virtually only the S domain (comprising the p24 monomer and its glycosylated derivative gp27), while yeast-derived vaccines successfully developed to date are composed exclusively of the S polypeptide (comprising exclusively the nonglycosylated p24 species).

The 22 nm HBsAg particles, have been purified from the plasma of chronic carriers. In terms of their plasma being particle-positive, these chronic carriers are referred to as HBs$^+$. If infected persons have mounted a sufficient immune response, they can clear the infection and become HBs$^-$. In terms of their formation of antibodies to HBs, these individuals are denoted anti-HBs$^+$. In this way, anti HBs$^+$ is correlated with recovery from disease and with immunity to reinfection from disease and with immunity to reinfection with HBV. Therefore, the stimulation or formation of anti-HBs by HB vaccines has been expected to confer protection against HBV infection.

This hypothesis has been testable experimentally. Outside of man, the chimpanzee is one of the few species which is fully susceptible to HBV infection, as reflected in quantifiable markers such as HBs$^+$ and elevated serum levels of liver enzyme. Chimpanzees have been vaccinated with three doses of purified HBsAg particles and then challenged intravenously with infectious HBV. While mock-vaccinated animals have shown signs of acute HBV infection, the HBsAg-vaccinated animals have been protected completely from signs of infection. Therefore, in this experimental system, HBsAg particles, composed of p24 (or p24 and p27), have been sufficient to induce protective immunity. Spurred by these observations, several manufacturers have produced EB vaccines composed of HBsAg particles.

In order to expand the available supply of HB vaccines, manufacturers have turned to recombinant DNA technology to mediate the expression of vital envelope proteins. Among microbial systems, *Escherichia coli* and *S. cerevisiae* have been used most commonly for the expression of many recombinant-derived proteins. Numerous attempts to express immunologically active HBsAg particles in *E. coli* have been unsuccessful. However, *S. cerevisiae* has shown great versatility in its ability to express immunologically active HBsAg particles. These particles (composed exclusively of p24), when formulated into a vaccine, have proven capable of fully protecting chimpanzees against challenge with live HBV of diverse serotypes. Furthermore, yeast-derived S particles are also immunologically active and as effective in preventing disease or infection in human clinical trials as plasma-derived HBsAg [Stevens et al., *JAMA*, 257:2612–2616 (1987)]. Therefore, the utility of *S. cerevisiae* as a host species for directing the synthesis of recombinant HBsAg is established firmly. In addition, expression of human therapeutic agents and vaccines in yeast can be very useful for product development, since yeast is free of endotoxin, is nonpathogenic to man, can be fermented to industrial scale, and lacks many of the safety concerns which surround the use of continuous mammalian cell lines (many of which are vitally transformed, may be tumorigenic in mice and all of which contain protooncogenes).

*S. cerevisiae* (bakers' yeast) is a eukaryote which is capable of synthesizing glycoproteins. Protein glycosylation in yeast has been the subject of numerous recent review articles [notably: Kukuruzinska et al., *Ann. Rev. Blochem.*, (1987) 56, 915–44; Tannen et al., BBA, (1987) 906, 81–99]. This glycosylation or additiion of glycans to appropriate receptor amino acids (aa) on the polypeptide occurs either at specific serine (Ser) or threonine (Thr) residues (O-linked) or at specified asparagine (Asn) residues (N-linked). The specificity for O-linked addition at Set or Thr residues is not clearly understood and is determined empirically on a case-by-case basis.

The signal sequence for N-linked glycosylation is well defined as either of the amino acid sequences Asn-X-Thr or Asn-X-Ser (wherein X is any amino acid). In addition to synthesizing many autologous, native, glycosylated proteins (among them being those called mannoproteins, or mannopeptides), yeast also are capable of glycosylating heterologous or foreign proteins expressed by recombinant technology (if the heterologous protein contains the appropriate glycosylation signal sequence for either N-linked or O-linked glycosylation).

The preS2+S polypeptides, which are produced during natural infection contain no more than two "core" [ca. 3 kilodaltons (kD) in size] N-linked glycans, one in the S region and a second on the Asn at amino acid residue 4 of the preS2 domain. The recognition site in the S domain is not glycosylated in either Recombivax HB® or in recombinant preS2+S synthesized in yeast. However, the site at amino acid residue 4 of the pzeS2 domain is recognized and glycosylated by yeast.

The preS1 domain contains an N-linked glycosylation site at amino acid residue 4 of the preS1 region and a potential site at aa residue 26 for serotype adw. It is readily apparent to those skilled in the art that arguments set forth for preS2 glycosylation also will follow for diverse sequences in the preS2 region as well as for those in the preS1 and S domains.

Yeast synthesizing recombinant preS2+S add a "core" glycan which is similar to that added to the native polypeptide during vital infection. However, if the yeast host cell is "wild-type" for glycosylation (i.e., containing the full complement of enzymes required for native glycosylation which is the case for virtually all commonly used yeast strains), a significant number of these glycans are extended with a large number of additional mannose residues in a manner identical to that employed by yeast in making its own structural mannoproteins. This extended addition of the glycan, when it occurs on a foreign gene product such as the preS2+S polypeptide, is referred to as hyperglycosylation. It is readily apparent to those skilled in the art that arguments set forth for yeast also will extend to other host cells (e.g., insect, fungi, etc.) which may be subject to divergent glycosylation patterns.

Furthermore, it has been demonstrated that recombinant forms of 22 nm particles of HBV surface proteins expressed in wild-type yeast host cells, entrap substantial amounts of yeast cell carbohydrate (deriving at least in part from the structural mannoproteins and mannopeptides of the yeast host cell) within the 22 nm particle. This entrapped carbohydrate could pose potential problems in that the entrapped carbohydrate may cause the generation of antibodies against yeast carbohydrate moieties on glycosylated proteins, and a vaccine immunogen containing entrapped yeast carbohydrate would react with anti-yeast antibodies present in most mammalian species thereby potentially diminishing its effectiveness as an immunogen and vaccine.

Hyperglycosylation and entrappment of complete mannoproteins and mannopeptides may be eliminated or glycosylation limited in HBV preS and S polypeptides, and their corresponding particles, by any of the following approaches.

Firstly, N-linked hyperglycosylation may be prevented or limited during growth of the recombinant host through the presence in the growth medium of an exogenous agent (e.g., tunicamycin). Secondly, polypeptides, from recombinant or natural sources may be deglycosylated either chemically (e.g. anhydrous tzifluoromethane-sulfonic acid or anhydrous hydrogen fluoride) or enzymatically (e.g., with N-glycanase, Endo-F or Endo-H) or physically (e.g. sonication). Thirdly, the recognition site for glycosylation may be changed or deleted by mutagenesis at the DNA level, such that core glycosylation, and thereby hyperglycosylation as well, is prevented. Such modified preS+S ORF's in which the glycosylation recognition sequence has been altered (directed by suitable promoters active in yeast) have been transformed into yeast host cells. The resultant preS+S polypeptides lack glycosylation. Fourthly, host cells may be identified which lack critical enzymes required for glycosylation, which illustrates the present invention without however limiting the same thereto. One such yeast strain has been identified (mnn9- mutant) [Ballou, L. et al., (1980), *J.Biol.Chem.*, 255, pp 5986–5991] which lacks a critical enzyme in the glycosylation pathway necessary for the elongation (hyperglycosylation) of the N-linked glycans; chemical studies indicate that this mutant makes mannoproteins without outer-chain mannose residues and containing only the "core" carbohydrate [Ballou, C. E. et al., (1986), *Proc. Natl. Acad. Sci. U.S.A.*, 83, pp 3081–3085; Tsai, P. et al., (1984), *J. Biol. Chem.*, 259, pp 3805–3811]. The ORF for the S or preS+S polypeptide (transcription directed by suitable promoters active in yeast) has been used to transform such mnn9- mutant yeast. The resulting preS+S polypeptide contains only "core" glycosylation and lacks hyperglycosylation.

Although the S polypeptides are neither glycosylated nor hyperglycosylated when expressed in yeast, particles composed therefrom contain significant levels of entrapped carbohydrate deriving from yeast mannopeptide. Therefore, the expression of S polypeptides as well as preS containing polypeptides in yeast cells which cannot hyperglycosylate results in decreased levels of carbohydrate in the expressed 22 nm particles.

*S. cerevisiae* has shown great versatility in its ability to express immunologically active 22 nm particles. These particles, when formulated into a vaccine, have proven capable of fully protecting chimpanzees against challenge with live HBV. Furthermore, yeast-derived HBsAg has been effective immunologically in human clinical trails as plasma-derived HBsAg. Therefore, the utility of *S. cerevisiae* as a host species for directing synthesis of recombinant HBsAg is established firmly.

In a variety of recombinant microbial expression systems, the synthesis of many different polpeptides has been shown to be deleterious to the host cell. As a consequence, there is selective pressure against the expression of such polypeptides, such that the only cells which accumulate in a scale-up of such a recombinant culture are those which have ceased to express the foreign polypeptide or express so little of the foreign polypeptide that the culture becomes an uneconomical source of that polypeptide. In some cases, the deleterious effect is so strong that when expression is driven by a strong constitutive promoter, newly transformed cells fail to propagate and form colonies on selective plates. These deleterious effects can be overcome by using an inducible promoter to direct the synthesis of such polypeptides. A number of inducible genes exist in *S. cerevisiae*. Four well-characterized inducible genetic systems are the galactose (GAL) utilization genes, the alcohol dehydrogenase 2 (ADH2) gene, the alpha mating factor gens, and the pho5 gene.

*S. cerevisiae* has 5 genes which encode the enzymes responsible for the utilization of galactose as a carbon source for growth. The GAL1, GAL2, GAL5, GAL7 and GAL10 genes respectively encode galactokinase, galacross permease, the major isozyme of phosphoglucomutase, α-D-galactose-1-phosphate uridyltransferase and uridine diphospho-galactose-4-epimerase. In the absence of galactose, very little expression of these enzymes is detected. If cells are grown on glucose and then galactose is added to the culture, these three enzymes are induced coordinately, by at least 1,000-fold, (except for GAL5, which is induced to about 5 fold) at the level of RNA transcription. The GAL1 GAL2, GAL5, GAL7 and GAL10 genes have been molecularly cloned and sequenced. The regulatory and promoter sequences to the 5' sides of the respective coding regions have been placed adjacent to the coding regions of the lacZ gens. These experiments have defined those promoter and regulatory sequences which are necessary and sufficient for galacross induction.

S. cerevisiae also has 3 genes, each of which encodes an isozyme of alcohol dehydrogenase (ADH). One of these enzymes, ADHII, is responsible for the ability of S. cerevisiae to utilize ethanol as a carbon source during oxidative growth. Expression of the ADH2 gene, which encodes the ADHII isozyme, is catabolite- repressed by glucose, such that there is virtually no transcription of the ADH2 gens during fermentative growth in the presence of glucose levels of 0.1% (w/v). Upon glucose depletion and in the presence of non-repressing carbon sources, transcription of the ADH2 gene is induced 100- to 1000-fold. This gene has been molecularly cloned and sequenced, and those regulatory and promoter sequences which are necessary and sufficient for derepression of transcription have been defined.

Alpha mating factor is a sex pheromone of S. cerevisiae which is required for mating between MATα and MATa cells. This tridecapeptide is expressed as a prepropheromone which is directed into the rough endoplasmic reticulum, glycosylated and pzoteolytically processed to its final mature form which is secreted from cells. This biochemical pathway has been exploited as an expression strategy for foreign polypeptides. The alpha mating factor gens has been molecularly cloned and its promoter with pre-pro-leader sequence has been utilized to express and secrete a variety of polypeptides. Likewise, the pho5 gene promoter has been shown to be inducible by low phosphate concentrations and this also has utility for physiologically regulated expression of foreign proteins in yeast.

As expected by their traversal of the rough endoplasmic reticulum and Golgi apparatus, foreign proteins can undergo both N- and O-linked glycosylation events. The alpha mating factor promoter is active only in cells which are phenotypically α. There are 4 genetic loci in S. cerevisiae, known as SIR, which synthesize proteins required for the repression of other normally silent copies of a and α information. Temperature-sensitive (ts) lesions which interfere with this repression event exist in the gene product of at least one of these loci. In this mutant, growth at 35° C. abrogates repression, resulting in cells phenotypically a/α in which the alpha mating factor promoter is inactive. Upon temperature shift to 23° C., the cells phenotypically revert to α such that the promoter becomes active. The use of strains with a ts SIR lesion has been demonstrated for the controlled expression of several foreign polypeptides.

OBJECTS OF THE INVENTION

It is an object of the present invention to provide a HBV surface protein which forms particles with substantially reduced entrapped carbohydrate content. It is another object of the present invention to provide a method of producing in a yeast host, HBV surface proteins which form particles and which contains substantially reduced entrapped carbohydrate content. An additional object of the present invention is to provide a vaccine against HBV comprising the HBV surface protein particles with substantially reduced entrapped carbohydrate content for both active and passive treatment of prevention of disease and/or infections caused by HBV or other agents serologically related to HBV. A further object of the present invention is to provide conditions for the large scale growth of recombinant host cells and the purification of the recombinant HBV surface proteins. These and other objects of the present invention will be apparent from the following description.

SUMMARY OF THE INVENTION

HBV surface proteins have been expressed at high yield in a recombinant yeast host which is genetically deficient in its ability to glycosylate proteins. The expression of HBV surface proteins in yeast cells results in the formation of the characteristic particles. Formation of these particles in yeast cells results in the entrapment of yeast cell substances within the particles. Using "wild-type" yeast host cells substantial amounts of yeast cell carbohydrate may become entrapped within the HBsAg particles. In order to circumvent the production of a HBV vaccine consisting of particles which contain substantial amounts of carbohydrate, the HBV surface proteins were produced and purified from a recombinant yeast host which is genetically deficient in its ability to glycosylate proteins. The HBV surface proteins produced by such a host form particles which contain substantially less carbohydrate than particles produced in wild-type yeast cells. These HBV surface proteins are useful as a vaccine for the treatment and/or prevention of HBV related infections, and as an antigen for immunologic diagnosis with reduced reactivity with naturally occuring anti-yeast antibodies.

DETAILED DESCRIPTION OF THE INVENTION

Figure 1:
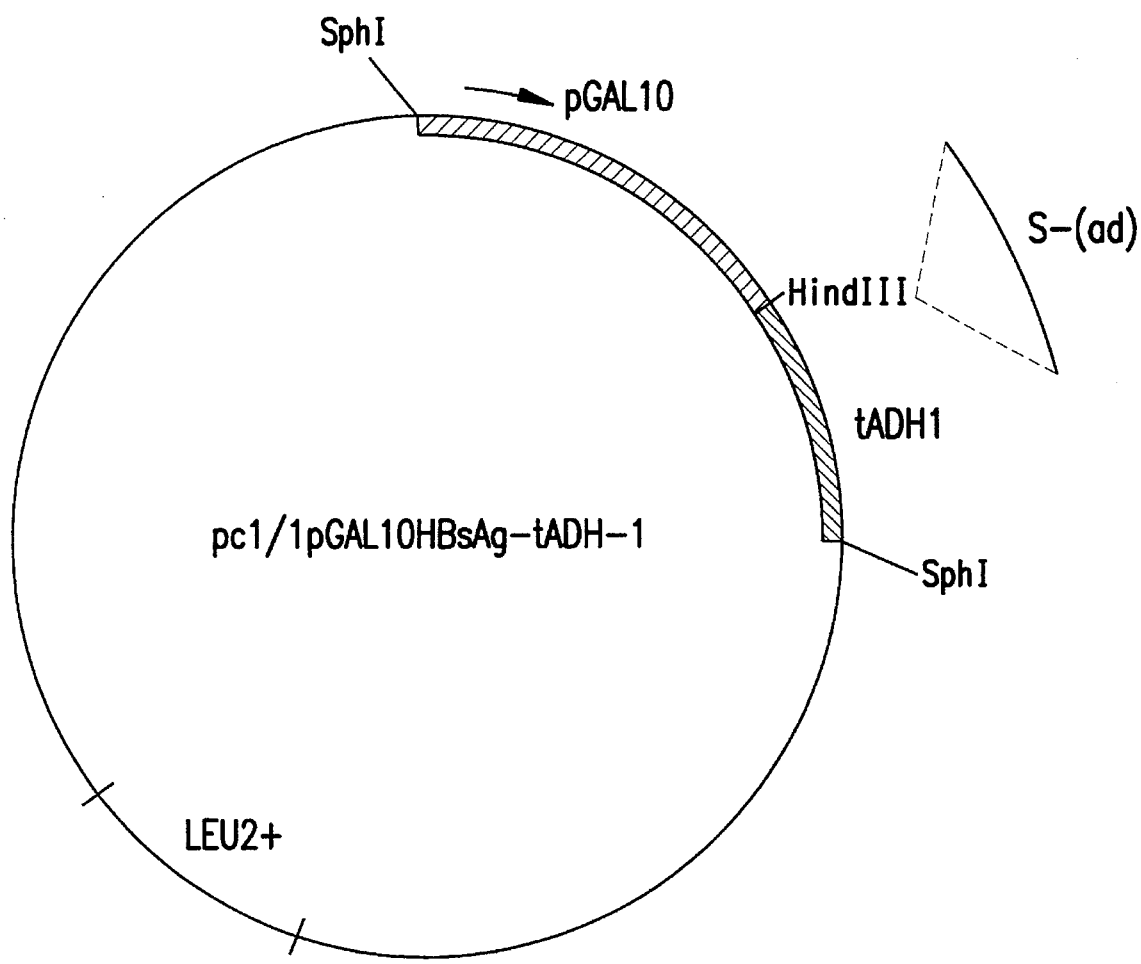
FIG. 1 shows schematically plasmid pCl/1pGAL10HBsAg-tADH-1 which contains the pGAL10 promoter driving transcription of the HBsAg ORF, followed by the tADH1 terminator, and the selectable marker LEU2+.

The present invention is directed to a method for the preparation of HBV surface protein particles which contain substantially reduced amounts of entrapped carbohydrate, for use as a vaccine against HBV.

Dane particles (serotype adw) were utilized as the source of HBV nucleic acid for the isolation of the vital ORFs. It is readily apparent to those skilled in the art that this invention extends to the use of nucleic acid from HBV strains or related viruses with other serologic reactivities which derive from viral genetic diversity. The endogenous polymerase reaction was employed in order to produce covalently-closed circular double-stranded DNA of the EBV genome from the nicked and gapped nucleic acid form that natively resides in the HB virion. The DNA was isolated, digested to completion with EcoRI, and cloned into the EcoRI site of pBR322, thus generating pHBV/ADW-1. The recombinant plasmids containing the HBV genome in a circularly permuted form at the EcoRI site of the PreS region were selected. The complete ORF encoding the 55 amino acids of the preS2 region, and the 226 amino acids of the S region was constructed first by purifying the 0.8 kilobase pair (kbp) fragment obtained following digestion of pHBV/ADW-1 with EcoRI and AccI; this fragment encodes the preS2+S polypeptide lacking only the initiation codon, the amino-terminal 3 amino acids, the carboxy-terminal 3 amino acids, and the translational terminator codon.

Oligonucleotides were synthesized and ligated to this fragment, converting it to a HindIII fragment containing a 10 bp yeast-derived non-translated 5' flanking sequence and the complete preS2+S ORF was chosen such that the termination codon was directly joined to a natural HindIII site in the ADHi transcriptional terminator, thus creating a completely native yeast-derived junction without any additional intervening bases. It is readily apparent to those skilled in the art that for expression of HBV surface and related proteins, any suitable yeast-active transcriptional terminator may be substituted for ADH1.

The 5' flanking sequence for the construction

ACAAAACAAA (SEQIDNO:1)
1           10

(SEQIDNO: 1) was chosen to correspond to that for the non-translated leader (NTL) of the yeast gene GAP63 (GAP) [Holland, *J. Biol. Chem.*, 225, 2596 (1980)] and is also a consensus for the GAP gene family. The construction was made in such manner as to join the NTL directly to the initiation codon of the preS2+S ORF without the intervention of any additional bases. Therefore, it is readily apparent to those skilled in the art that, for expression of HBV surface proteins, the selection of NTL sequences extends to other sequences which result in suitable expression levels.

DNA sequence analysis revealed 2 base substitutions which resulted in amino acid differences from the preS2+S sequence encoded by the DNA of pHBpreSGAP347/19T [Valenzuela et al., *Biotechnology*, 3(4), 317–320 (1985)]. In order to evaluate indentical polypeptides for both constructions, these nucleotide substitutions, which were T instead of C at base 64 of the 846 bp ORF of HBV preS2+S (encoding Phe rather than Leu) and C instead of A at base 352 (encoding His rather than Gln) were changed by site-directed mutagenesis [Zoller et al., *Nucleic Acids Research* $LQ$:6487–6500 (1982)]. The encoded amino acid sequence for the optimized construction then was verified. It is readily apparent to those skilled in the art that this invention is not limited to this sequence and extends to any sequence wherein the DNA encodes a polypsprides with HBV-related antigenicity.

The large DNA fragment of 3.3kbp which contains pUC19 and the HBsAg coding region was separated from the preS2 encoding DNA fragment after digestion with EcoRI and StyI, and purified by preparative agarose gel electrophoresis. A synthetic DNA oligonucleotide was then ligated with the pUC19-HBsAg fragment. This synthetic DNA oligonucleotide contains 5' EcoRI and 3' StyI sticky ends as well as providing a HindIII site immediately following the 5' EcoRI site. In addition, the synthetic DNA oligonucleotide contains the HBsAg ATG codon plus the 9 upstream nucleotides and the 21 downstream nucleotides including the StyI site.

This oligonucleotide rebuilds the complete coding region of the HBsAg and allows its subsequent removal intact, from the pUC19 based vector by digestion with HindIII.

The pUC19-EBsAg DNA fragment with the ligated synthetic DNA olgonucleotide described above was used to transform *E. coli*. Recombinant plasmids were selected which possess the complete reconstructed HBsAg coding region. The complete HBsAg open reading frame (ORF) was removed from the recombinant plasmid by digestion with HindIII followed by isolation and purification of the 0.7 kbp HBsAg DNA by preparative agarose gel electrophoresis for cloning into a GAL10 promoter expression vector.

The expression cassette (pGAL10-tADH1) drives expression of foreign genes inserted at a unique HindIII site down stream from the galactose-inducible GAL10 promoter. The EBsAg ORF (with HindIII termini) described above was ligated into the HindIII site of the vector. This expression cassette was inserted between the SphI sites of the *E. coli* shuttle vector pCl/1 (Beggs, supra) and this vector was introduced into *S. cerevisiae* strains CF52 or CF54 and transformed clones were selected.

Following mutagenesis, the fragment encoding either S or preS+S described above was used to construct an expression cassette, as described previously [Kniskern et al., *Gene* 46:135–141, (1986)], which was composed of: (a) ca. 1.1 kbp of the GAP491 promoter, (b) a 10 bp yeast-derived flanking sequence, (c) 1230 bp of the vital ORF for preS1+preS2+S or 846 base pairs of the vital ORF for preS2+S or 681 bp of the vital ORF for S, and (d) ca. 0.4 kbp of the yeast ADH1 terminator.

Three different expression vectors were used to construct HBsAg expression cassettes. The GAP 491 promoter expression cassette described previously [Kniskern et al., 1986 *Gene* 46 pp135–141], is composed of about 1.1 kbp of the glyceraldehyde-3-phosphate dehydrogenase (GAPDE) promoter and about 350 bp of the yeast alcohol dehydrogenase I (ADH1) terminator in a pBR322 backbone, with a unique HindIII site between the promoter and terminator. The HBsAg ORF from Example 2 was ligated in the unique HindIII site, and its presence and orientation confirmed by restriction endonuclease analyses and Southern blot.

Alternately the (0.5 Skbp) GAL10 promoter (Schultz etal., 1987, *Gene,* 54, pp113–123) was substituted for the 1.1 kbp GAP promoter in the above construction, or the (1.25 kbp) ADH2 promoter (Kniskern et al., 1988 *Hepatology* 8, 82–87) was substituted for the GAP promoter (see FIG. 1).

In each case, the expression cassette containing the specific promoter, the HBsAg ORF, and the ADS1 terminator was cloned into the shuttle vector pCl/1 (Beggs, supra; Rosenberg, et al., supra) to create a yeast expression vector which was then used to transform *S. cerevisiae* as described below. These transformants were established as frozen stocks for evaluation and subsequent experimentation. Parental strain CF52 was obtained as follows: The α mating type strain CZS/LB347-1C (mnn9$^-$, SUCZ$^-$) was mated with the a type strain 2150-2-3 (leu2$^-$, ade1$^-$) by mixing the strains on a YEHD complete media plate. To select for diploids, the mated strains were replica plated onto leu$^-$ minimal medium containing 2% sucrose as the sole carbon source. After isolating single colonies, the diploids were sporulated, and asci were dissected by standard techniques. The KHY-107 strain was isolated as a single spore and characterized as cir$^+$, ade1$^+$, leu2$^-$, and mnn9$^-$ (by Schiff stain technique).

KEY107 (cir 0) was derived from strain KHY107 (cir$^+$) as described by Broach [Methods in Enzymology, 101, Part C, pp 307–325, (1983)]. The cured strain was made ura3$^-$ by integrating a disrupted ura3 gene. The resulting strain, KHY-107ura3Δ, was grown in rich media to allow the accumulation of spontaneous mutations and a canavanine resistant mutant was selected. The mutant strain, CF55, was shown by complementation tests to be can1[31]. The GAL10pGAL4 expression cassette was integrated into the HIS3 gens of CF55 (*Methods in Enzymology*, 1990, 185 pp297–309) to yield the final host strain CF52 (Mata leu2-2,112 ura3Δ can1 his3Δ::GAL10pGAL4-URA3, cir°). These transformants were established as frozen stocks for evaluation and subsequent experimentation.

Recombinant yeast from the frozen stocks was grown in YEHD medium [Catty et al., *J. Industrial Micro.*, 2, 117–121, (1987)]. After growth to stationary phase, yeast cells were harvested. Lysates were prepared, resolved by sodium dodecylsulfate-polyacrylamide gel electrophoresis (SDS-PAGE), and immunoblotted with antibodies to HBsAg. One polypeptide was found with molecular weight of about 24-kD in accord with the predicted molecular weight of the translational product of the S ORF. Furthermore, lysates of recombinant, but not parental, yeast were positive for S by radioimmunoassay (Ausria®). Electron microscopic examination of partially purified yeast lysates showed high densities of typical HBsAg particles.

The yeast-derived promoter initiates transcription of the HBsAg and related genes. Therefore, it is readily apparent to those skilled in the art that any yeast-active promoter sequence (e.g. including by not limited to GAL1, GAL10, ADH2 Pho5, etc.) may be substituted for the GAP491 promoter. It is also readily apparent to those skilled in the art that a suitable assay system, e.g., immunoblot or RIA or enzyme-linked immunoassay (EIA), should be utilized in order to assay expression of HBsAg and related polypeptides in this system, such that the time of harvesting of the culture for attaining a maximal yield can be optimized.

The GAP491 promoter has been useful for the expression in yeast of several foreign proteins, including HBsAg [Bitter et al., *Gene*, 32:263–274, (1984); Wampler et al., *Proc, Nat. Acad. Sci. USA*, 82:6830–6834, (1985)]. Based upon our previous results of expressing HBcAg to about 40% of soluble yeast protein (Kniskern et al., supra), we have used this promoter to drive the expression of HBsAg and related proteins in suitable yeast host cells.

It is readily apparent to those skilled in the art that the selection of a suitable yeast strain for expression of HBV surface proteins encompasses a wide variety of candidates. Suitable yeast strains include but are not limited to those with genetic and phenotypic characteristics such as protease deficiencies, and altered glycosylation capabilities.

In order to control and define the glycosylation of recombinant yeast-expressed HBV proteins, *S. cerevisiae* strain CF52 (Mata leu2-2,112 ura3Δ can1 his3Δ:: GAL10pGAL4-ura3, cir°) which was constructed as described above.

The expression plasmid pCl/1pGAL10HBsAg-tADH-1 was used to transform CF52 (Mata leu2-2,112 ura3Δ can1 his3Δ:: GAL10pGAL4-ura3, cir°). Transformed clones were selected on minimal medium (leu−) containing 1M sorbitol. These cloned transformants were established as frozen stocks in 17% glycerol for subsequent evaluation and further experimentation.

To provide a glycosylation wild-type control, the expression plasmid was also used to transform yeast strain CF54, which was isolated by established techniques from strain CF52, and which is a spontaneous revertant to MNN9+ (and thus is wild-type for glycosylation but otherwise is of identical genotype to strain CF52). Transformed clonal isolates were established as frozen stocks in 17% glycerol for subsequent evaluation and further experimentation.

Clones of transformed yeast containing the expression plasmids were plated onto leu⁻ selective agar plates (containing 1M sorbitol for mnn9-transformants) and incubated at 30° C. for 2–3 days. These yeast were inoculated into 5–7 mL cultures of complex FEED (Carry et al., supra) medium (containing 0.1–1M sorbitol), plus 2% galactose for GAL10 based plasmids, and the cultures were incubated at 30° C. with aeration for 12–18 hours. Flasks containing 50 mL complex YEHD medium with 1M sorbitol (hereafter called YEHDS) were inoculated from the above cultures (to an initial $A_{600}$=0.1) and were incubated at 30° C. with shaking (350 rpm) for 48–72 hours to a final $A_{600}$ of 10–16. Samples of 10 $A_{600}$ units were dispensed into tubes, and the yeast cells were pelleted by centrifugation at 2000×g for 10 minutes. Samples either were assayed directly or stored frozen at −70° C. At the time of assay, the pellets were resuspended in 0.4 mL of phosphate- buffered saline (PBS) containing 2mM phenylmethyl sulfonyl fluoride (PMSF) and transferred to 1.5 mL Eppendorf tubes. Yeast cells were broken by: 1) the addition of 200–300 mg of washed glass beads (0.45 mm) and agitation on a vortex mixer for 15 minutes, 2) addition of TRITON X-100 to 0.5%, 3) agitation on the vortex mixer for 2 minutes, and 4) incubation at 4° C. for 10 minutes. Cellular debris and glass beads were removed and the supernatant assayed for protein [by the method of Lowry et al., *J. Biol. Chem.*, 193, 265, (1951)] and RIA specific for preS2+S [Hansson et al., *Infect Immunol.* 26: 125–130, (1979), Machida et al., *Gastroenterology* 86: 910–918, (1984)] or S (AUSRIA®).

Clones of transformed yeast mnn9- containing the expression plasmids were plated onto (leu−) selective agar plates containing 1M sorbitol and incubated at 30° C. for 2–3 days. These yeast were inoculated into 5–7 mL cultures of complex YEHDS media (plus 2% galactose for GAL10 promoter plasmids), and the cultures were incubated from the above cultures (to an initial $A_{600}$=0.1) and were incubated at 30° C. with shaking (350 rpm) for 48–72 hours to a final $A_{600}$ of 10–16. Triplicate samples of 10 $A_{600}$ units were dispensed into tubes, and the yeast cells were pelleted by centrifugation at 2000×g for 10 minutes. Samples either were assayed directly as described above or stored frozen at −70° C.

Immunoblot analysis of the polypeptide derived from all recombinant clones described above, in host cells with the mnn9- phenotype, showed one band with apparent molecular size of about 24-kD.

For recombinant proteins, the qualitative and quantitative glycosylation patterns are a function of and largely dependent upon the host cell species, and within a species upon the cell line. It is thus readily apparent to those skilled in the art that the selection of a host strain extends to species and cell lines other than *S. cerevisiae* for which mutations in enzymes in the glycosylation pathway may be identified. It is also readily apparent to those skilled in the art that selection of host strains of *S. cerevisiae* extends to all strains in which mutations in enzymes of the glycosylation pathway may be identifed.

The transformed clones were then screened for the presence of the HBsAg DNA and expression of p24 HBsAg. Cells were grown in YEHDS medium (also containing galacross for the GAL10 promoter plasmids to induce expression following glucose depletion). Lysates were prepared, resolved by sodium dodecyl sulfate-polyacrylamide gel electrophoresis (SDS-PAGE) and Western blotted to nitrocellulose. A p24 product was found to be specific to S protein by virtue of its presence only in induced transformants and its reactivity with anti-p24 serum. One of these clones was selected for further analysis. Furthermore, lysates of transformants, but no parental *S. cerevisiae*, were positive for HBsAg by radioimmunoassay.

This highlights the utility of the expression vector which utilizes the GAL10 promoter to direct the expression of HBsAg and related surface proteins in *S. cerevisiae*. It is readily apparent to those skilled in the art that the regulatable GAL10 promoter, or GAL1, GAL2, GAL7 or MEL1 promoters which function in an indistinguishable manner, enable the growth of a recombinant *S. cervisiae* culture to be scaled up to a production-scale volume before synthesis of the recombinant protein is initiated, such that negative effects on the host cell are minimized. Moreover, it is readily apparent to those skilled in the art that an expression vector containing another regulatory promoter, including but not limited to ADH2 and alpha mating factor, physiologically inducible or derepressible by other means, can be utilized to direct expression of S and preS-containing peptides. Furthermore, it is readily apparent to those skilled in the art that a constitutive promoter less potent than GAPDH, including but not limited to CYC1, drives expression of S and pre-S-containing polypeptides to a lower percentage of cell protein, such that the negative physiological effects of overexpression would be obviated. It is readily apparent to those skilled in the art that a suitable assay system, e.g., Western blot or radioimmunoassay, should be utilized in order to assay expression of S and pre-S-containing polypeptides in this system so that the time of harvesting of the culture for attaining a maximal yield can be optimized.

An immune-affinity column, bound with goat antibodies which recognize the particulate form of HBsAg, has been utilized to purify S and S-related proteins from transformed *S. cerevisiae*. The eluted product is positive for HBsAg by radioimmunoassay, and is of particulate form in electron microscopy. Such a particulate form which contains both HBsAg and pre-S antigens or HBsAg alone is effective as a HBV vaccine and diagnostic reagent.

Yeast cells transformed with expression vectors coding for a hepatitis B virus surface protein or variants thereof are grown and harvested. The cells may be stored if desired by washing the cells in a buffer solution, e.g. PBS, and forming a cell paste which is typically stored frozen at −70° C.

Purification of HBsAg and related proteins typically begins as follows. A batch of fresh or frozen cell paste is suspended in a buffer, preferably TRIS, at a high pH ranging between about 8.5 and about 11.0, preferrably about 10.5 (the buffer may also contain suitable protease inhibitors). The cells are then disrupted, preferably by mechanical means. The gentle bead breakage method of disruption has been found to be unsuitable for scale-up use. Disruption by a high pressure homogenizer (about 10,000 to 20,000 psi, using a Gaulin or Stansted homogenizer) is preferred because of its rapid and efficient operation.

Disruption of the yeast cells results in a crude extract. The crude extract is then pH adjusted. The pH is adjusted to within the range of 8.0 to 11.0, with 10.5 being preferred.

It may be desired at this point to add a detergent to the crude extract. The addition of a detergent will facilitate the separation of yeast cell membranes from unwanted cellular debris. It has been shown that preS2+S protein, as well as other forms of the surface proteins, may associate with yeast cell membranes. A variety of neutral or non-ionic detergents can be used, including but not limited to detergents of the TRITON-N series, TRITON-X series, BRIJ series, TWEEN series or EMASOL series, deoxycholate, octylglucopyranoside or NONIDET-Np-40. Zwitterionic detergents such as CHAPS or CHAPSO are also useful and suitable agents.

If a detergent is to be used, the preferred detergent is TRITON X-100 at a concentration of about 0.5%. It must be stressed that the method of this invention does not require detergent use at this step and the use of detergents is optional.

The extract then may be heat treated if protease inhibitors are not present during lysis. Heat treatment is effective over a range of temperatures and for a range of treatment duration. Typically a temperature range of 45° C. to 60° C. is used, with 50° C. as the preferred temperature. The duration of heat treatment typically ranges between 20 to 40 minutes with 30 minutes as the preferred time. The extract is heat treated in a suitable vessel and the vessel is immersed in a heated bath, or a heat exchanger is used. The material is then cooled to about 10° C., preferably by placing it into an ice-water bath or by using a heat exchanger. It will be readily apparent to those skilled in the art that, according to the method of this invention, the order in which the heat treatment and the debris removal steps are done may be reversed without significant effect on the result of this procedure. Alternatively, whole yeast cells can be heated in a neutral pH buffer, disrupted and detergent added as described above.

Removal of cellular debris from the heat treated crude extract is necessary to prevent physical occlusion during subsequent purification steps. Debris can be removed by centrifugation, microfiltration, or filtration producing a clarified extract. Centrifugation and microfiltration are the most preferred methods. Centrifugation can be done for varying lengths of time at different centrifugal forces. Centrifugation at about 3,000×g for 15 minutes at 4° C. has been found adequate. It may also be advantageous to dilute the extract before centrifugation to reduce the typically viscous nature of a crude yeast cell extract. Dilution will not alter any subsequent steps of this procedure.

Microfiltration has an advantage in that filtration and dialysis can be performed simultaneously. Several types of microfiltration units are suitable for use in this step, e.g. KROSFLO by Microgon Inc. or any variety of hollow fiber cartridges by Amicon or A/G Technology. The preferred microfiltration method is to pass the extract through Prostak Durapore (Millipore) membrane, plate and frame microfiltration unit with a pore size of about 0.1 microns to 0.2 microns, at an inlet pressure of about 2 to 7 psi, using a buffer consisting of about 0.1M TRIS, pH about 10.4 and about 0.1% TRITON X-100.

The supernatant from centrifugation or the filtrate from microfiltration may be concentrated prior to the next step of this procedure. Concentration can be achieved by several methods including, but not limited to, dialysis, filtration, lyophilization, ultrafiltration and diafiltration. The preferred method of concentration of the present invention is to run the clarified extract through a $10^5$ molecular weight cut off, hollow fiber ultrafiltration system. The volume of the clarified extract is typically reduced by about 6.5 fold for the microfiltration product and about 2 fold for the diluted, centrifuged product, yielding a concentrated retentate. Following concentration, the retentate is defiltered to further remove lower molecular weight contaminants. Diafiltration is performed using a $10^5$ molecular weight cutoff, hollow fiber system.

If TRITON X-100 was added, it can be removed by several conventional methods including, but not limited to, dialysis, addition of certain organic solvents, refrigeration, chromatographic separation, and contact with a gel or resin which specifically binds detergents, such as Extractogel (Pierce) and XAD resin (Romicon). The preferred method of this invention to remove TRITON X-100 is to circulate the heat treated extract containing TRITON X-100 through a cartridge of XAD-2 or XAD-4 resin (polystyrene divinylbenzene). The heat treated extract is circulated through the XAD cartridge for about 10 hours at 4° C. and then collected in a suitable vessel, for example, a sealable glass bottle.

If the cells were disrupted in a high pH buffer, the pH of the heat treated extract, or the extract containing protease inhibitors, is then adjusted to between about pH 7.0 to about 7.9 with the preferred pH of about 7.7. Adjusting the pH to about 7.7 following heat treatment at a high pH according to the method of this invention, greatly facilitates the adsorption of envelope proteins to the wide pore silica utilized in a subsequent step. Adjustment of the pH of the heat treated extract can be performed prior to the Triton X-100 removal step without effecting the outcome of the procedure. Therefore, it will be obvious to those skilled in the art that, according to the method of this invention, the order in which the pH adjustment and the Triton X-100 removal steps are done may be reversed without significant effect on the result of this procedure.

The HBsAg is then easily separated from the contaminants yielding substantially purified HBsAg. The preferred method of eliminating the contaminants is to adsorb the HBsAg onto wide pore silica. The most preferred method of this invention is to adsorb the HBsAG onto a wide pore silica with a pore size range of about 1000 to 1500 angsttoms and silica particle size range of about 30 to 130 microns (Amicon). The surface protein readily enters the pores of the silica and is retained. The yeast cellular protein contaminants can therefore be easily washed away.

Adsorption of surface protein onto wide pore silica can be done chromatographically or in a non-chromatographic, batchwise fashion. Chromatographic adsorption is done by passing the pH adjusted extract through a bed of wide pore silica in a column chromatography apparatus. Typically, about one liter of heat treated extract is applied to a 5 cm jacketted column apparatus containing about 300 ml (about 100 g dry weight) of wide pore silica beads at a flow rate of about 200 ml/hour.

Non-chromatographic adsorption onto wide pore silica is typically done by mixing the heat treated extract with the silica in a suitable vessel, e.g. a sealable glass bottle. The preferred method is to add 300 ml of wide pore silica to about one liter of heat treated extract in a glass bottle and incubate with constant mixing. Adsorption preferrably continues for about 1.5 hours at about 4°–8° C. although different times and temperatures are suitable.

Washing of the surface protein-adsorbed silica free of unadsorbed material can also be done non-chromatographically, or the silica can be poured into a column apparatus, as previously described, for chromatographic adsorption. Batchwise washing is done by draining the heat treated extract from the wide pore silica and adding several volumes of a buffer which will not cause the release of HBsAg adsorbed onto the silica. The preferred buffer is PBS. The silica is drained and the washing steps are repeated 3 to 5 times.

Chromatographic washing of the surface protein-adsorbed silica is done by passing PBS through the silica at a flow rate of about 200 ml/hour until the extinction at 280 nm is constant.

The HBsAg is eluted from the washed wide pore silica using a buffer solution with a pH between about 8.5 to 9.0. Surface proteins are preferably desorbed using a buffer solution consisting of about 0.05M Borate at a pH of about 8.7. Desorption of EBsAg can be facilitated at elevated temperatures over a wide range. Desorption at about 55° C. is preferred.

Non-chromatographic desorption is done by mixing 1200 ml of 0.05M Borate buffer at pH 8.7 with about 700 ml of washed HBsAg-adsorbed wide pore silica. Desorption continues for about 25 minutes. The eluate is then collected, the desorption steps are repeated twice and the eluate is cooled.

Chromatographic desorption is done by warming the jacketted column of washed silica to about 55° C. The 0.05M Borate buffer at pH 8.7 is warmed to 55° C. and then applied to the column at a rate of 500 ml/hour. The eluate is then collected and cooled. The volume of eluate is usually roughly equivalent to the volume of heat treated extract applied to the wide pore silica.

Concentration of the eluted HBsAg is usually desired. The preferred concentration method is to pass the eluate through a $10^5$ molecular weight cut-off hollow fiber diafiltration system using a 0.05M Borate buffer, pH 8.7. The volume of the eluted surface protein may be generally reduced by as much as 16 fold using this system. The diafiltration retentate can be sterilized by microfiltration if necessary.

The carbohydrate content of the HBsAg is determined by the method of Dubois, M. et al., Anal. Chem., 28, pp.350, 1956. The general principle of this procedure is that simple sugars, oligosaccharides, polysaccharides and their derivatives, including the methyl ethers with free or potentially free reducing groups, give an orange yellow color when treated with phenol and concentrated sulfuric acid. The mount of color produced at a constant phenol concentration is proportional to the amount of sugar present.

To determine the carbohydrate content of a sample of HBV surface proteins, 1 mL of a solution containing between 10 to 70 µg of protein is placed in a test tube. A series of carbohydrate standards and blank samples are prepared. One mL of a 5% phenol solution is added to each tube, the tubes are mixed, and 5 mL of a 96% sulfuric acid solution is added and mixed. The tubes are incubated at room temperature for 10 minutes, mixed, and incubated at 25° to 30° C. for 20 minutes. The samples are read in spectrophotometer ($A_{490}$ for hexoses and methylated hexoses, and $A_{480}$ for penroses, uronic acid, and their methylated derivatives) and the amount of carbohydrate in the HBsAg samples is determined by comparison with the carbohydrate standards.

HBsAg produced in "wild-type" recombinant yeast cells (CF54), and HBsAg produced in the CF52 recombinant yeast cells were both analyzed for carbohydrate content as described above. Based on these results, a ratio of the amount of carbohydrate to protein present in each sample was calculated by dividing the micrograms of carbohydrate by the micrograms of protein in the sample. This ratio calculation demonstrated that HBsAg produced in $mnn9^-$ recombinant yeast cells consistently contained one tenth of the carbohydrate content of HBsAg produced in recombinant "wild-type" yeast cells. These results show that HBsAg produced in the $mnn9^-$ mutant yeast cells contained substantially reduced amounts of carbohydrate when compared to HBsAg produced in "wild-type" yeast cells.

The following examples illustrate the present invention without, however, limiting the same thereto. The disclosure of each reference mentioned in the following examples is hereby incorporated by reference.

EXAMPLE 1

Cloning of HBVDNA in pBR322

HBV Dane particles (serotype adw) were isolated and purified from human plasma (carrier), and double-stranded DNA was synthesized by the endogenous polymerass in the Dane particles according to the methods of Landers et al., [*J. Virology,* 23, 368–376, (1977)] and Hruska et al., [*J. Virology,* 21, (1977)]. The DNA was isolated after digestion with Proteinass K in SDS followed by extraction with phenol/chloroform and ethanol precipitation. The HBV genomic DNA was digested with EcoRI, producing a single 3.2 kbp fragment, that was cloned into the EcoRI site of pBR322 to form pHBV/ADW-1. The presence of the HBV DNA was confirmed by EcoRI digestion, Southern blot transfer to nitrocellulose, and hybridization with [³²P]-labelled specific oligonucleotide probes.

EXAMPLE 2

Cloning of the preS2+S Gene into the pGAP-tADH-2 Expression Vector

Plasmid pHBV/ADW-1 (described in Example 1) was digested with EcoRI and AccI, and the 0.8 kbp fragment was purified by preparative agarose gel electrophoresis. Also, a DUC plasmid was digested with EcoRI and BamHI and the linear vector was purified by preparative agarose gel electrophoresis.

To reconstruct the 5' portion of the preS2+S ORF, a pair of oligonucleotides was synthesized which reconstitutes the ORF from the EcoRI site upstream to the ATG through a 10 bp NTL sequence through a HindIII site to an EcoRI terminus. The sequence of these oligonucleotides are:

```
AATTCAAGCT TACAAAACAA AATGCAGTGG (SEQIDNO: 4)
1         10         20        30

GTTCGAATGT TTTGTTTTAC GTCACCTTAA (SEQIDNO: 3)
1         10         20        30
```

To reconstitute the 3' portion of the preS2+S ORF, a second pair of oligonucleotides was synthesized which reconstitutes the ORF from the AccI site through the translational terminator through a HindIII site to a BamHI terminus. The sequence of these oligonucleotides are:

```
ATACATTTA AGCTTG (SEQIDNO: 4)
1         10   15

TGTAAATTTC GAACCTAG (SEQIDNO:5)
10        10       18
```

The oligonucleotide pairs were annealled, then ligated to the pUC EcoRI-BamHI digested vector. The resultant vector (2.8 kbp) was purified by preparative agarose gel electrophoresis. The 0.8 kbp EcoRI-AccI fragment from above was ligated with this vector. The presence and orientation of the PreS2+S ORF was confirmed by restriction endonuclease analysis and Southern blot. DNA sequence analysis [Sanger et al., 1977] revealed two base substitutions that resulted in amino acid differences from the sequence encoded by the DNA of plasmid EBpreSGAP347/19T. To evaluate identical polypeptides for both constructions, these substituions, which were T instead of C at base 64 (encoding Phe rather than Leu) and C instead of A at base 352 (encoding His rather than Gln), were changed by site-directed mutagenesis. [Zoller and Smith 1982, Nucleic Acids Research, 10, pp6487–6500].

A plasmid containing the HBsAg coding region without the preS2 coding region was constructed as follows: The pUCHBpreS2+S plasmid (described above) was digested with EcoRI and StyI restriction endonucleases. The large DNA fragment (3.3 kbp) which contains pUC and the HBsAg coding region was separated from the preS2 encoding DNA fragment and purified by preparative agarose gel electrophoresis. A synthetic DNA oligonucleotide pair:

```
AATTCAAGCT TACAAAACAA AATGGAGAAC ATCACATCAG GATTC (SEQIDNO: 6)
1         10         20         30         40   45

GTTCGAATGT TTTGTTTTAC CTCTTGTAGT GTAGTCCTAA GGATC (SEQIDNO: 7)
1         10         20         30         40   45
``` was then ligated with the pUCHBsAg fragment. This synthetic oligonucleotide pair contains 5' EcoRI and 3' StyI sticky ends as well as providing a HindIII site immediately following the 5' EcoRI site. In addition, the synthetic DNA oligonucleotide pair contains the HBsAg ATG codon, the upstream 10 bp non-translated leader sequence, and the 21 downstream nucleotides including the StyI site.

This oligonucleotide pair rebuilds the complete coding region of the HBsAg and allows its subsequent removal intact, from the pUC based vector by digestion with HindIII.

The pUC-HBsAg DNA vector with the ligated DNA oligonucleotide pair described above was used to transform E. coli. Recombinant plasmids were selected which possess the complete reconstructed HBsAg coding region. The complete HBsAg open reading frame (ORF) was removed from the recombinant plasmid by digestion with HindIII followed by isolation and purification of the (0.7 kbp) HBsAg DNA by preparative agarose gel electrophoresis for cloning in to an expression vector.

EXAMPLE 3

Cloning of HBsAg ORF into 3 different expression vectors

Three different expression vectors were used to construct ]tBsAg expression cassettes. The GAP 491 promoter expression cassette described previously [Kniskern et al., 1986 Gene 46 pp135–141], is composed of about 1.1 kbp of the glyceraldehyde-3-phosphate dehydrogenase (GAPDH) promoter and about 350 bp of the yeast alcohol dehydrogenase I (ADH1) terminator in a pBR322 backbone, with a unique HindIII site between the promoter and terminator. The HBsAg ORF from Example 2 was ligated in the unique HindIII site, and its presence and orientation was confirmed by restriction endonuclease analyses and Southern blot.

Alternately the (0.5 kbp) GAL10 promoter (Schultz et al., 1987, Gene, 54, pp113–123) was substituted for the 1.1 kbp GAP promoter in the above construction, and the (1.25 kbp) ADH2 promoter (Kniskern et al., 1988 Hepatology 8, 82–87) was substituted for the GAP promoter (see FIG. 1).

In each case, the expression cassette containing the specific promoter, the HBsAg ORF, and the ADH1 terminator was cloned into the shuttle vector pCl/1 (Beggs, supra; Rosenberg, et al., supra) to create a yeast expression vector which was then used to transform S. cerevisiae as described below.

EXAMPLE 4

Construction of yeast S. Cerevisiae CF52 (mnn9–) mutant yeast strain

Yeast S. cerevisiae strain KEY 107 (cir⁺, ade1⁺, leu2⁻ and mnn9-) was constructed as follows: The α mating type strain CZ5/LB347-1C (mnn9⁻, SUCZ⁻) was mated with the a type strain 2150-2-3 (leu2⁻, ade1⁻) by mixing the strains on a YEHD complete media plate. To select for diploids, the mated strains were replica plated onto leu⁻ minimal medium containing 2% sucrose as the sole carbon source. After isolating single colonies, the diploids were sporulated, and asci were dissected by standard techniques. The KHY-107 strain was isolated as a single spore and characterized as cir+, ade1+, leu2−, and mnn9− (by Schiff stain technique).

KHY107 (cir 0) was derived from strain KHY107 (cir+) as described by Broach [*Methods in Enzymology*, 101, Part C, pp 307–325, (1983)]. The cured strain was made ura3− by integrating a disrupted ura3 gene. The resulting strain, KHY-107ura3Δ, was grown in rich media to allow the accumulation of spontaneous mutations and a canavanine resistant mutant was selected. The mutant strain, CF55, was shown by complementation tests to be can1−. The GAL10pGAL4 expression cassette was integrated into the HIS3 gens of CF55 (*Methods in Enzymology*, 1990, 185 pp297–309) to yield the final host strain CF52 (Mata leu2-2, ura3Δcan1 his3Δ::GAL10pGAL4-URA3, cir°).

EXAMPLE 5

Yeast Transformation and Seed Establishment for HBsAg in CF52 mnn9−Mutant Yeast

The pCl/1 pGAL10HBsAg-tADH-1 plasmid described in Example 3 was used to transform *S. cerevisiae* strain CF52. Clones were selected on minimal medium (leu- containing 1M sorbitol), established as frozen stocks (in 17% glycerol) and evaluated as described below.

EXAMPLE 6

Growth and Expression of the HBsAg Gene behind the GAL10 promoter in Yeast CF52 (mnn9$^{-1}$)

Clones of yeast containing the expression plasmid described in Example 5 above were plated onto leu− selective agar plates containing 1M sorbitol and incubated at 30° C. for 2-3 days. These yeast were inoculated with 5–7 mL of complex YEHDS (YEHD+1M sorbitol) and the cultures were incubated at 30° C. with aeration for 12–18 hours. Flasks containing 50 mL YEHDS+2% galactose media were inoculated from the above culture (to an initial $A_{600}$=0.1) and incubated at 30° C. with shaking (350 rpm) for 72 hours to a final $A_{600}$ of 10–16. Samples of 10 $A_{600}$ units were dispensed into tubes, and the yeast cells were pelleted at 2,000×g for 10 minutes. The pellets either were assayed directly or stored at −70° C. for future assay. At the time of assay, the pellets were resuspended in 0.4 mL of phosphate-buffered saline containing 2mM PMSF. Yeast cells were broken 1) the addition of 200–300 mg of washed glass beads (0.45 mm), 2) agitation on a vortex mixer for 15 minutes, 3) addition of TritonX-100 to 0.5% (v/v), 4) agitation on a vortex mixer for 2 minutes, and 5) incubation at 4° C. for 10–15 minutes. Cellular debris and glass beads were removed by centrifugation at 13,000×g for 10 minutes. The clarified supernatant fluid was removed and analyzed for protein [by the method of Lowry et al., *J. Biol. Chem.*, 193,265 (1951)] and for HBsAg by (AUSRIA®) assay (Abbott). Typical assay results are shown below.

TABLE I

| SAMPLE DESCRIPTION Shake Flasks | AUSRIA. UG/MG PROTEIN | BREAKAGE | P24 LEVEL (IMMUNO- BLOT) |
|---|---|---|---|
| mnn9− mutant | (0.55, 0.61, 0.53) | Glass beads | +++ |
| wild type (MNN9+) | (1.8) | Glass beads | + |

EXAMPLE 7

Large Scale Growth of *S. cerevisiae* (mnn9−) Producing HBsAz in Fermentors

The frozen recombinant yeast culture was inoculated onto leu− plates containing 1M sorbitol. The plates were incubated inverted at 28° C. for 2–3 days. The growth on the plates was resuspended in YEHDS and the resuspended growth was transferred into 2-L Erlenmeyer flask containing 500 mL of YEHDS, and 2% galacross. The flask was incubated at 28° C. and 350 rpm in a controlled environment shaker incubator for 18–22 hours. These seed cultures then were used to inoculate the production stage vessels.

An inoculum (1–5% v/v) from one or more flasks was transferred into 16-L or 250-L fermentors containing 10-L or 200-L of YEHDS, respectively. The 16-L fermentors were operated at 500 rpm, 5 L/min air, and 28° C. The 250-L fermentors were operated at 160 RPM, 60 L/min air and 28° C. The fermentors were harvested 40–46 hrs after inoculation with the seed culture. Optical density values of 15.0 A660 units typically were obtained. Harvesting consisted of concentrating the cells using a hollow fiber filtering device followed by washing the cells in buffered salt solutions. Cell slurries were assayed as described below or stored frozen at −70° C for further processing and analysis.

Small samples (0.6 mL) of 20% washed cell slurries were broken using glass beads (0.45–0.52 mm) in 1.5-mL Eppendorf tubes. PMSF (6.5 µl of 200 mM stock) was added as a protease inhibitor. Aliquots were removed from the tubes after breakage and frozen at −70° C. for immunoblot analysis. TRITON X-100 was added to the remaining sample in the tubes to a final concentration of 0.5%, and the samples were mixed briefly and incubated at 4° C. for 20–40 min. The cell debris was removed by centrifugation and the clarified cell extract assayed for antigen (Ausria®) and protein (Lowry).

EXAMPLE 8

Purification of S protein in particulate form by means of immune affinity chromatography Recombinant *S. cerevisiae*, constructed as described in Example 5, were grown in either flasks or fermentors. The yeast cells were harvested by microfiltration in an Amicon DC-10 unit, suspended in 30 ml buffer A [0.1M $Na_2HPO_4$, pH 7.2, 0.5M NaCl], and broken in a Stansted pressure cell for seven passages at 75–85 pounds per square inch. The broken cell suspension (31 gm wet cell weight) was diluted with 120 ml buffer A, Triton X-100 was added to a final concentration of 0.5% (w/v), and the suspension was clarified by centrifugation at 10,000×g for 20 min. at 4° C. The clarified broth was decanted and incubated with Sepharose 4B coupled with antibodies to HBsAg [McAleer et al., *Nature* 307: 178 (1984)] for 19 hours at 4° C to adsorb the antigen onto the resin. After the incubation period, the slurry was warmed to room temperature for all subsequent steps and degassed under vacuum for 15 min. The degassed slurry was poured into a 2.5×40 cm column. When the column had been packed fully, unbound protein was washed away with buffer A. The antigen was eluted with 3M KSCN in buffer A. Fractions containing antigen were dialyzed against 0.007M $Na_2HPO_4$, pH 7.2, 0.15M NaCl at 4° C. and pooled to form the Dialyzed Affinity Pool containing 1.08 mg of protein in 20 ml. Sixteen ml of Dialyzed Affinity Pool was diluted to 40 mcg/ml with 5.6 ml 0.006M $Na_2HPO_4$, pH 7.2, 0.15M NaCl. The product was sterilized by filtration through a Millex-GV 0.22µ membrane. The identity of the product in the Dialyzed Affinity Pool was verified by the detection of HBsAg by Ausria® reactivity.

TABLE II

| SAMPLE DESCRIPTION Fermenters | AUSRIA, UG/MG/ PROTEIN | BREAKAGE |
|---|---|---|
| mnn9– | (1.13, 1.10, 1.06) | Glass Beads |
| mnn9– | (3.1, 4.4) | Manton-Gaulin |
| wild-type | (3.3) | Manton-Gaulin |

EXAMPLE 9

Large Scale Purification of Recombinant HBsAg

About 250 g of frozen cell paste (producing recombinant S protein) was resuspended to 17% wet weight/volume (about 1500 ml) in phosphate buffered saline solution (PBS). The cells were heated to 45° C. by immersion in a water bath. The cells were held at 45° C. for 15 minutes and then cooled on ice to about 10° C. The cells were then disrupted by two passages through a Gaulin homogenizer.

Following homogenization, 10% Triton X-100 was added to a final concentration of 0.3% and mixed for about 15 minutes. The cell extract was then centrifuged at 3,600×g for 20 minutes at 4° C., and the supernatant was collected.

The supernatant was then passaged over a column containing about 200 g of XAD-2 resin to remove the Triton X-100. The effluent was then passaged directly over a column containing about 150 g of wide pore silica with a pore size of about 1,500 angstrom and a particle size of about 50 microns. The columns used were 5 cm diameter (Pharmacia) and were run at a flow rate of about 200 ml per hour.

The silica column was washed with PBS until the $A_{280}$ returned to baseline.

The S protein was eluted from the silica column using first, cold borate buffer (50 mM, pH 8.7, 4° C.) at a flow rate of about 500 ml per hour, until a rise in the A280 was observed. Once the $A_{280}$ began to rise the column was heated to 55° C. and 55° C. borate buffer was run through the column at about 500 ml per hour. The eluate containing S protein (about 1L) was collected on ice. The eluate was then concentrated to about 200 ml by diafiltration against 50 mM borate buffer at pH 8.7, using a hollow fiber diafiltration unit with a molecular weight cutoff of $10^5$. The S protein was then filtered through a 0.2 micron filter and stored. The product was found to be stable with no significant degradation observed on Western blot analysis.

EXAMPLE 10

Assay of Carbohydrate Content of the Recombinant HBV Surface Proteins

The carbohydrate content of the recombinant HBV surface proteins was determined by the method of Dubois, M. et al., *Anal. Chem.*, 28, pp.350, 1956. The general principle of this procedure is that simple sugars, oligosaccharides, polysaccharides and their derivatives, including the methyl ethers with free or potentially free reducing groups, give an orange yellow color when treated with phenol and concentrated sulfuric acid. The amount of color produced at a constant phenol concentration is proportional to the amount of sugar present.

To determine the carbohydrate content of HBsAg produced in wild-type yeast strain and produced in the mnn9⁻ yeast strain, 1 mL of a solution containing between 10 to 70 μg of protein was placed in a test tube. A series of carbohydrate standards and blank samples were prepared containing various amounts of carbohydrate. Ons mL of a 5% phenol solution was added to each tube, the tubes were mixed, and 5 mL of a 96% sulfuric acid solution was added and mixed. The tubes were incubated at room temperature for 10 minutes, mixed, and incubated at 25° to 30° C. for 20 minutes. The samples were read in spectrophotometer ($A_{490}$ for hexoses and methylated hexoses, and $A_{480}$ for penroses, uronic acid, and their methylated derivatives) and the amount of carbohydrate in the HBV surface protein samples was determined by comparison with the carbohydrate standards.

Based on these results, a ratio of the amount of carbohydrate to protein present in each sample was calculated by dividing the micrograms of carbohydrate by the micrograms of protein in the sample, which is shown below.

| Carbohydrate-to-protein ratio of HBsAg | |
|---|---|
| Yeast strain | Carbohydrate/Protein |
| mnn9⁻ | 0.05 |
| wild-type for glycosylation (MNN9+) | 0.56 |

This ratio calculation demonstrated that HBsAg produced in mnn9⁻ recombinant yeast cells consistently contained one tenth of the carbohydrate content of HBsAg produced in recombinant "wild-type" yeast cells. These results show that HBsAg produced in the mnn9⁻ mutant yeast cells contained substantially reduced amounts of carbohydrate when compared to HBsAg produced in "wild-type" yeast cells.

What is claimed is:

1. A process for producing HBsAg particles comprising the S antigen with an entrapped carbohydrate content to protein ratio of less than about 0.5 comprising:
    (a) culturing a yeast cell containing an expression vector encoding the S FIBsAg, said yeast cell being defective in its ability to glycosylate proteins; and
    (b) purifying particles of S HBsAg expressed by said cultured yeast cell.

2. The process of claim 1 wherein said yeast cell is *Saccharomyces cerevisiae.*

3. The process of claim 2 wherein said *Saccharomyces cervisae* is mnn9 defective.

4. A process for producing HBsAg particles comprising the S antigen with an entrapped carbohydrate content to protein ratio of less than about 0.5 comprising:
    (a) transforming a yeast cell that is defective in its ability to glycosylate proteins with an expression vector encoding the S HBsAg;
    (b) culturing said transformed yeast cell under conditions that result in expression of particles of the S HBsAg; and
    (b) purifying particles of S HBsAg expressed by said cultured yeast cell.

5. The process of claim 4 wherein the level of entrapped carbohydrate is reduced by a factor of about ten fold as compared to the level of carbohydrate present when said HBsAg particles are expressed in a glycosylation competent yeast cell.

* * * * *